(12) United States Patent
Wang et al.

(10) Patent No.: US 11,426,310 B2
(45) Date of Patent: Aug. 30, 2022

(54) ABSORBENT ARTICLE HAVING ELASTIC BELT

(71) Applicant: The Procter & Gamble Company, Cincinnati, OH (US)

(72) Inventors: Xuechun Wang, Beijing (CN); Koichi Morimoto, Beijing (CN); Hui Liu, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 365 days.

(21) Appl. No.: 16/550,406

(22) Filed: Aug. 26, 2019

(65) Prior Publication Data

US 2019/0374403 A1 Dec. 12, 2019

Related U.S. Application Data

(63) Continuation of application No. PCT/CN2017/074994, filed on Feb. 27, 2017, and a
(Continued)

(51) Int. Cl.
*A61F 13/49* (2006.01)
*A61F 13/496* (2006.01)
(Continued)

(52) U.S. Cl.
CPC .... *A61F 13/49061* (2013.01); *A61F 13/4902* (2013.01); *A61F 13/49012* (2013.01);
(Continued)

(58) Field of Classification Search
CPC .. A61F 2013/15373; A61F 2013/15382; A61F 2013/49022; A61F 2013/49025; A61F 13/49012; A61F 13/49011
See application file for complete search history.

(56) References Cited

U.S. PATENT DOCUMENTS 7,901,393 B2  3/2011 Matsuda et al.
8,298,205 B2  10/2012 Norrby et al.
(Continued)

FOREIGN PATENT DOCUMENTS

CN  101106962 A  1/2008
CN  101795650 A  8/2010
(Continued)

OTHER PUBLICATIONS

International Search Report and Written Opinion, PCT/CN2017/105983, dated Jan. 15, 2018.
(Continued)

*Primary Examiner* — Susan S Su
(74) *Attorney, Agent, or Firm* — Charles R. Matson; Richard L. Alexander

(57) ABSTRACT

Disclosed is an absorbent article continuous in a longitudinal direction and a transverse direction comprising a front elastic belt region, a back elastic belt region, a crotch region, a waist opening and two leg openings; the front and back elastic belt regions being a laminate comprising an inner sheet made of nonwoven fiber, and an outer sheet made of nonwoven fiber, and a plurality of elastic bodies configured to stretch the front and back elastic belt regions in the transverse direction, the outer sheet having a material caliper of at least about 0.25 mm at 500. Pa; the article further comprising a topsheet, a backsheet, and an absorbent core disposed between the topsheet and the backsheet; the absorbent core existing through the entire longitudinal dimension of the crotch region and extending at least partly in the back elastic belt region; the back elastic belt region having a maximum caliper MaxBC and a minimum caliper MinBC according to the measurements herein, wherein the difference between the MaxBC and the MinBC is no greater than about 5 mm.

15 Claims, 7 Drawing Sheets

Related U.S. Application Data continuation-in-part of application No. PCT/CN2017/105983, filed on Oct. 13, 2017.

(51) Int. Cl.
*A61F 13/511* (2006.01)
*A61F 13/84* (2006.01)
*A61F 13/515* (2006.01)
*A61F 13/51* (2006.01)
*A61F 13/15* (2006.01)
*A61F 13/514* (2006.01)

(52) U.S. Cl.
CPC .... *A61F 13/4963* (2013.01); *A61F 13/51121* (2013.01); *A61F 13/84* (2013.01); *A61F 13/515* (2013.01); *A61F 13/5148* (2013.01); *A61F 2013/15373* (2013.01); *A61F 2013/49022* (2013.01); *A61F 2013/49025* (2013.01); *A61F 2013/49034* (2013.01); *A61F 2013/49093* (2013.01); *A61F 2013/51028* (2013.01); *A61F 2013/8497* (2013.01)

(56) References Cited

U.S. PATENT DOCUMENTS

| | | | |
|---|---|---|---|
| 8,622,983 B2 | 1/2014 | Wilkes et al. | |
| 9,060,903 B2 | 6/2015 | Takeuchi et al. | |
| 9,220,643 B2 | 12/2015 | Mariko et al. | |
| 9,421,134 B2 | 8/2016 | Schlinz et al. | |
| 9,549,859 B2 | 1/2017 | Wilkes et al. | |
| 2003/0139713 A1* | 7/2003 | Olson | A61F 13/15203 604/385.01 |
| 2004/0102757 A1 | 5/2004 | Olson | |
| 2004/0243083 A1 | 12/2004 | Matsuda et al. | |
| 2005/0107763 A1 | 5/2005 | Matsuda | |
| 2006/0030831 A1 | 2/2006 | Matsuda et al. | |
| 2010/0076394 A1 | 3/2010 | Hayase | |
| 2011/0160692 A1 | 6/2011 | Wilkes et al. | |
| 2012/0029460 A1* | 2/2012 | Yamashita | A61F 13/4902 604/385.26 |
| 2013/0310798 A1 | 11/2013 | Glahn | |
| 2014/0088542 A1 | 3/2014 | Wilkes et al. | |
| 2014/0332436 A1 | 11/2014 | Sasayama et al. | |
| 2016/0184145 A1 | 6/2016 | Morimoto | |
| 2016/0331600 A1 | 11/2016 | Polidori et al. | |
| 2017/0156945 A1* | 6/2017 | Hashimoto | A61F 13/515 |
| 2017/0165128 A1 | 6/2017 | Morimoto et al. | |
| 2017/0189244 A1 | 7/2017 | Mueller et al. | |
| 2017/0335498 A1 | 11/2017 | Hansen et al. | |
| 2018/0168885 A1 | 6/2018 | Zink et al. | |

FOREIGN PATENT DOCUMENTS

| | | |
|---|---|---|
| CN | 203885725 U | 10/2014 |
| CN | 105167916 A | 12/2015 |
| EP | 3326596 | 5/2018 |
| JP | 2008508082 A | 3/2008 |
| JP | 2016067435 A5 | 7/2017 |
| WO | 2014208639 A1 | 12/2014 |
| WO | 2015064606 A1 | 5/2015 |
| WO | 2016011197 A2 | 1/2016 |
| WO | 2016029374 A1 | 3/2016 |
| WO | 2016029566 A1 | 3/2016 |
| WO | 2016101196 A1 | 6/2016 |
| WO | 2016114947 A1 | 7/2016 |
| WO | WO2016168997 | 10/2016 |

OTHER PUBLICATIONS

International Search Report and Written Opinion; Application Ser. No. PCT/CN2017/074994, dated Nov. 30, 2017, 8 pages.
PCT Suppl. Search Report and Written Opinion for PCT/US2017/105983 dated Jun. 17, 2019, 12 pages.

\* cited by examiner

ABSORBENT ARTICLE HAVING ELASTIC BELT

CROSS REFERENCE TO RELATED APPLICATION

This application is a continuation, under 35 USC 120, of Application No. PCT/CN2017/074994, filed on Feb. 27, 2017 and Application No. PCT/CN2017/105983, filed on Oct. 13, 2017, both of which are herein incorporated by reference in their entirety.

FIELD OF THE INVENTION

The present invention relates to absorbent articles having an elastic belt region having a smooth transition from the waist opening to the region having an absorbent core.

BACKGROUND OF THE INVENTION

Infants and other incontinent individuals wear absorbent articles such as diapers to receive and contain urine and other body exudates. Pull-on absorbent articles, or pant-type absorbent articles, are those which are donned by inserting the wearer's legs into the leg openings and sliding the article up into position about the lower torso. Pant-type absorbent articles have become popular for use on children who are able to walk and often who are toilet training, as well as for younger children who become more active in movement such that application of taped-type absorbent articles tends to be more difficult, and also for younger babies requiring a soft fit around the waist opening and leg openings.

Pant-type articles may take various structures wherein the circumference of the waist opening and vicinity thereof is made elastic enough to facilitate the wearer or the caregiver to expand the article and insert the wearer's legs into the leg openings for wearing the article. The region of the waist circumference and vicinity thereof is often referred to as the elastic belt. One type of structure for the pant-type article is the belt-type pant having a main body to cover the crotch region of the wearer and a separate elastic belt defining the waist opening and leg opening, such as described in PCT Publication WO 2006/17718A. Another type of structure for the pant-type article is the uni-body pant configured such that the outer cover of the article completely covers the entirety of the garment-facing surface of the article, wherein the portion configured to stretch about the torso is considered the elastic belt region.

Whatever the structure of the pant-type article may be, the elastic belt region may be the portion which is most touched and observed by the wearer or the caregiver upon use, and thus its properties most associated with the function and quality of the article. By function, what may be desired is an elastic belt region which is easily stretchable, provides a comfortable yet reliable fit, and provides a sufficient containment capacity. By quality, what may be desired is an undergarment-like integral appearance and feel. Negative factors for achieving the undergarment-like appearance and feel include, for example, conspicuousness of the absorbent core. Negative factors for achieving the overall integral impression may include conspicuousness of other discrete parts which form the absorbent article.

Based on the foregoing, there is a need for an absorbent article having improved undergarment-like integral appearance and feel without compromise to fit or containment capacity.

SUMMARY OF THE INVENTION

The present invention is directed to an absorbent article continuous in a longitudinal direction and a transverse direction comprising a front elastic belt region, a back elastic belt region, a crotch region, a waist opening and two leg openings;

the front and back elastic belt regions being a laminate comprising an inner sheet made of nonwoven fiber, and an outer sheet made of nonwoven fiber, and a plurality of elastic bodies configured to stretch the front and back elastic belt regions in the transverse direction, the outer sheet having a material caliper of at least about 0.25 mm at 500 Pa;

the article further comprising a topsheet, a backsheet, and an absorbent core disposed between the topsheet and the backsheet; the absorbent core existing through the entire longitudinal dimension of the crotch region and extending at least partly in the back elastic belt region;

the back elastic belt region having a maximum caliper MaxBC and a minimum caliper MinBC according to the measurements herein, wherein the difference between the MaxBC and the MinBC is no greater than about 5 mm.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings and which like designations are used to designate substantially identical elements, and in which:

DEFINITIONS

Figure 1:
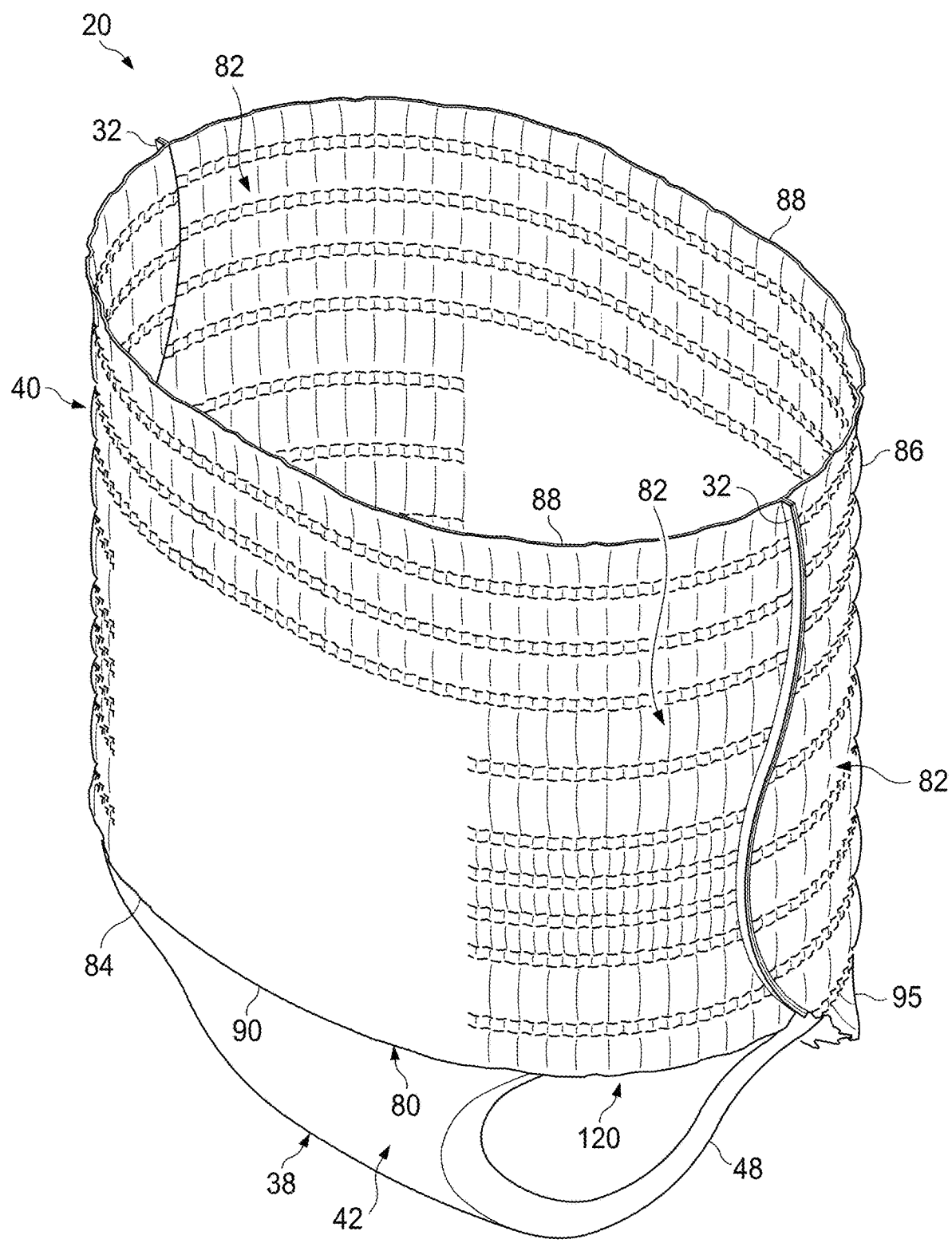
FIG. 1 is a perspective view of one embodiment of an absorbent article of the present invention.

As used herein, the following terms shall have the meaning specified thereafter:

"Absorbent article" refers to articles of wear which may be in the form of pants, taped diapers, incontinent briefs, feminine hygiene garments, and the like. The "absorbent article" is so configured to also absorb and contain various exudates such as urine, feces, and menses discharged from the body.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants".

"Longitudinal" refers to a direction running substantially perpendicular from a waist edge to an opposing waist edge of the article and generally parallel to the maximum linear dimension of the article.

"Transverse" refers to a direction perpendicular to the longitudinal direction.

"Proximal" and "distal" refer respectively to the position closer or farther relative to the longitudinal center of the article.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable".

"Extendibility" and "extensible" mean that the width or length of the component in a relaxed state can be extended or increased.

"Elasticated" and "elasticized" mean that a component comprises at least a portion made of elastic material.

"Elongatable material", "extensible material", or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

"Artwork" refers to a visual presentation to the naked eye, which is provided by printing or otherwise, and having a color. Printing includes various methods and apparatus well known to those skilled in the art such as lithographic, screen printing, flexographic, and gravure ink jet printing techniques.

"Color" or "Colored" as referred to herein includes any primary color except color white, i.e., black, red, blue, violet, orange, yellow, green, and indigo as well as any declination thereof or mixture thereof. The color white is defined as those colors having a $L^*$ value of at least 94, an $a^*$ value equal to 0±2, and a $b^*$ value equal to 0±2 according to the CIE $L^*$ $a^*$ $b^*$ color system.

DETAILED DESCRIPTION OF THE INVENTION

Figure 2:
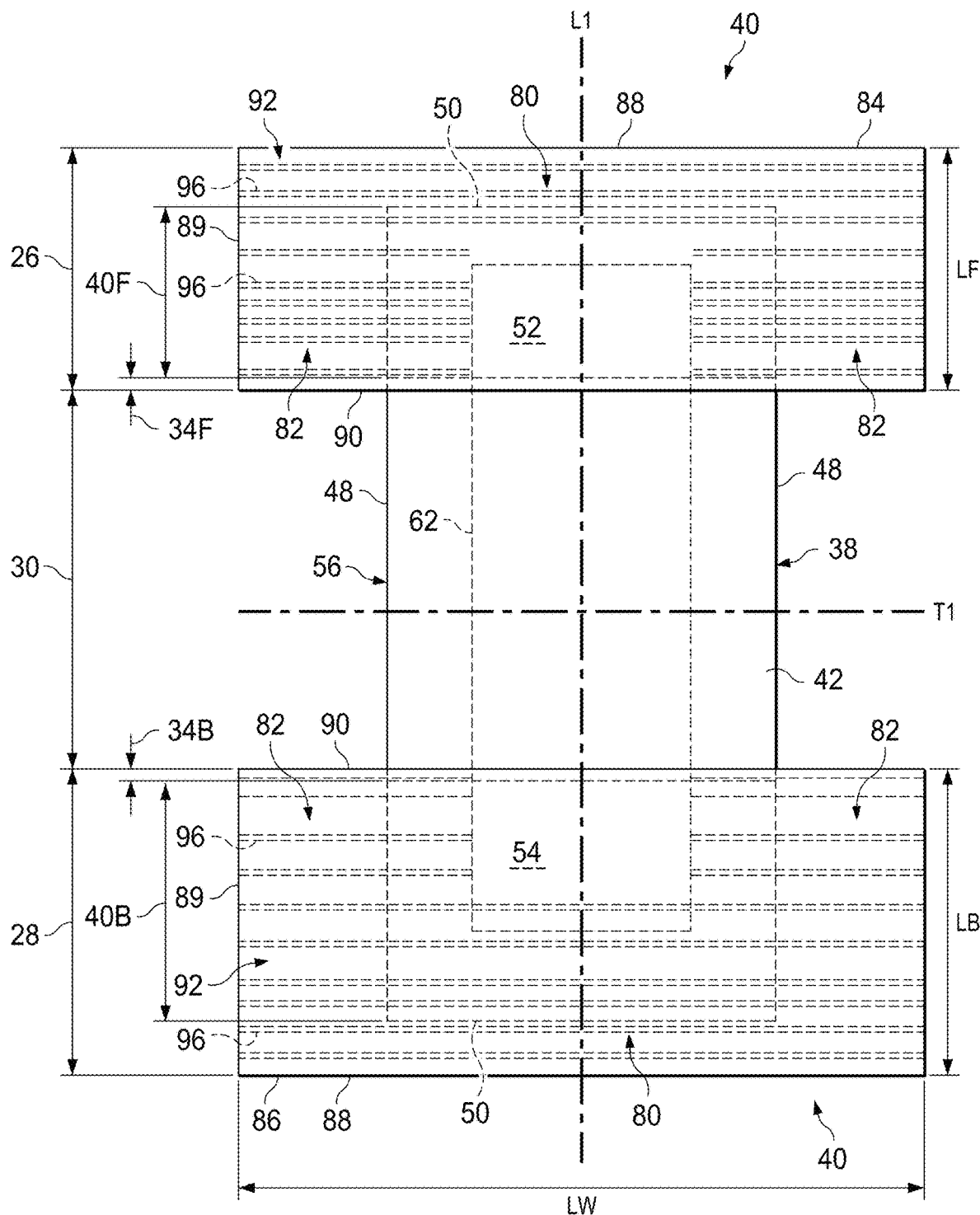
FIG. 2 is a schematic plan view of one embodiment of an absorbent article of the present invention with the seams enjoined and in a flat uncontracted condition showing the garment facing surface.

FIG. 1 is a perspective view of an embodiment of the absorbent article 20 of the present invention and FIG. 2 is a schematic plan view of the same article with the seams unjoined and in its flat uncontracted condition showing the garment-facing surface. The absorbent article 20 has a longitudinal centerline L1 which also serves as the longitudinal axis, and a transverse centerline T1 which also serves as the transverse axis. The absorbent article 20 has a body facing surface, a garment facing surface, a front region 26, a back region 28, a crotch region 30, and side seams 32 which join the front region 26 and the back region 28 to form two leg openings and a waist opening. The absorbent article 20 may be a belt-type pant comprising a core chassis 38 to cover the crotch region of the wearer, a front belt 84 and a back belt 86 (hereinafter may be referred to as "front and back belts"), the front and back belts 84, 86 forming a discrete ring-like elastic belt 40 (hereinafter may be referred to as "waist belt") extending transversely defining the waist opening. For the belt-type pant, the discrete ring-like elastic belt 40 may also be referred to as the elastic belt region 40. For the belt-type pant, the front and back belts 84, 86 and the core chassis 38 jointly define the leg openings. The absorbent article 20 may be a uni-body type pant wherein the core chassis 38 is continuous with the front and back belt 84, 86, wherein the leg openings are continuously formed. For the uni-body pant, the belt portion existing between the side seams are considered the elastic belt region 40, wherein the elastic belt region 40 is considered to terminate by an imaginary line running in the transverse direction between the proximal edges of the side seams. The remainder of the article except the elastic belt region 40 is considered the crotch region 30.

Figure 3:
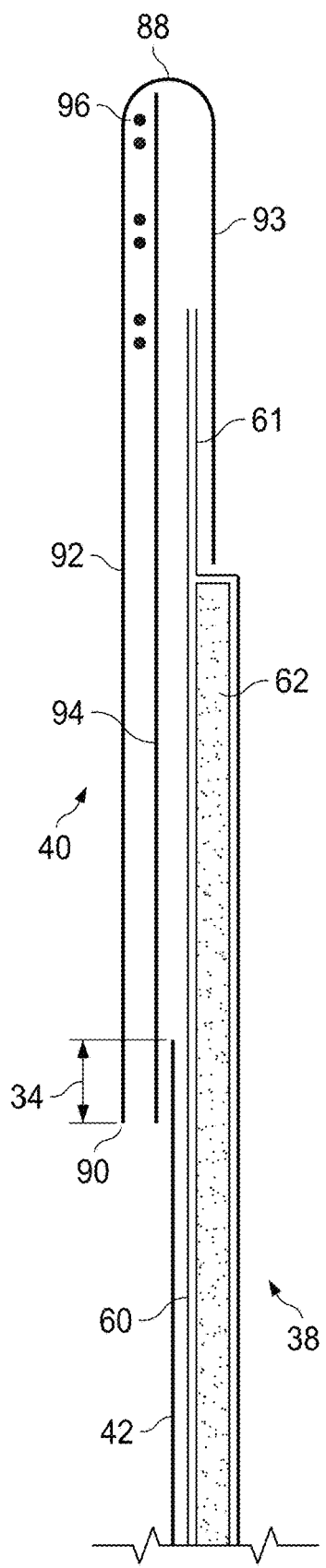
FIG. 3 is a cross section view of FIG. 2 taken along the longitudinal center line.

Referring to FIG. 3, the core chassis 38 comprises a topsheet, a backsheet 60 and an absorbent core 62 disposed between the topsheet and the backsheet 60, and further an outer cover layer 42 for covering the garment-facing side of the backsheet 60. The topsheet may be a water permeable substrate. The backsheet 60 may be a water impermeable film. The outer cover layer 42 may be a nonwoven sheet. The core chassis 38 contains an absorbent core 62 for absorbing and containing body exudates disposed on the core chassis 38, and an absorbent material non-existing region 61 surrounding the periphery of the absorbent core 62. The absorbent material non-existing region 61 may be made of the topsheet and/or the backsheet 60 and/or the outer cover layer 42 and/or other parts configuring the core chassis 38. Referring to FIG. 2, the core chassis 38 may have a generally rectangular shape, left and right longitudinally extending side edges 48 (hereinafter may be referred to as "side edge") and front and back transversely extending end edges 50 (hereinafter may be referred to as "end edge"). The absorbent core 62 exists through the entire longitudinal dimension of the crotch region and extending at least partly in the back elastic belt region; or at least partly in both the front and back elastic belt region. The core chassis 38 also has a front waist panel 52 positioned in the front region 26 of the absorbent article 20, a back waist panel 54 positioned in the back region 28, and a crotch panel 56 between the front and back waist panels 52, 54 in the crotch region 30. The center of the front belt 84 is joined to a front waist panel 52 of the core chassis 38, the center of the back belt 86 is joined to a back waist panel 54 of the core chassis 38, the front and back belts 84, 86 each having a left side panel and a right side panel 82 where the core chassis 38 does not overlap. The core chassis has a crotch panel 56 positioned between the front waist panel 52 and the back waist panel 54. The front and back belt may be discontinuous of each other in the longitudinal direction.

The absorbent core 62 may include an absorbent layer and an acquisition layer. The absorbent layer is the region wherein absorbent materials having a high retention capacity, such as superabsorbent polymers, are present. The absorbent layer may be substantially cellulose free. Superabsorbent polymers of the absorbent layer may be disposed between first and second layers of material immobilized by a fibrous layer of thermoplastic adhesive material. The first and second layers of materials may be nonwoven fibrous webs including synthetic fibers, such as mono-constituent fibers of PE, PET and PP, multiconstituent fibers such as side by side, core/sheath or island in the sea type fibers. Such synthetic fibers may be formed via a spunbonding process or a meltblowing process. The acquisition layer facilitates the acquisition and the distribution of body exudates and may be placed between the topsheet and the absorbent layer. The acquisition layer may include cellulosic fibers.

The absorbent layers may be disposed in plurality in the absorbent core 62. Some portions of the absorbent layers may be configured to have substantially no absorbent material to form channels. Channels may be useful for allowing the absorbent core to bend upon swelling with fluids, such that the absorbent article conforms to the wearer's body after swelling and prevent sagging of the article. The channels may also be formed in the acquisition layer, and may be configured to at least partly match the channels of the absorbent layer in the thickness direction.

The vicinity of the longitudinal side edges 48 of the core chassis 38 may be formed into a pair of outer cuffs extending transversely outward from the core chassis 38. The outer cuffs may be partly made by a cuff material, and comprise cuff elastic members. The core chassis 38 may further comprise a pair of inner cuffs extending toward the body facing side. The inner cuffs may be partly made by a cuff material, and comprise cuff elastic members.

The elastic belt region of the article of the present invention acts to dynamically create fitment forces and to distribute the forces dynamically generated during wear. The proximal edge 90 is located closer than the distal edge 88 relative to the crotch panel 56 of the core chassis 38. The front and back belts 84, 86 may be joined with each other only at the side edges 89 at the seams 32 to form an absorbent article having a waist opening and two leg openings. Each leg opening may be provided with elasticity around the perimeter of the leg opening. For the belt-type pant, the elasticity around the leg opening may be provided by the combination of elasticity from the front belt 84, the back belt 86, and any from the core chassis 38.

The transverse width of the backsheet 60 and the outer cover layer 42 may be the same, or may be varied (not shown). For example, the backsheet 60 may have a shorter transverse width compared to that of the outer cover layer 42. By such configuration, the longitudinal side edges 48 of the crotch panel 56, which make part of the leg openings, may have better breathability. Further, such configuration may provide cost saving.

The front belt 84 and back belt 86 are configured to impart elasticity to the belt 40. The front belt 84 and the back belt 86 may each be formed by a laminate comprising a plurality of elastic bodies 96 configured to stretch the front and back elastic belt regions in the transverse direction, an inner sheet 94, an outer sheet 92, and an outer sheet fold over 93 wherein the outer sheet fold over 93 is an extension of the outer sheet material formed by folding the outer sheet material at the distal edge 88 of the front and back belts; wherein the belt elastic bodies 96 are sandwiched between two of these sheets. The front belt 84 and the back belt 86 may each be made only by elastic bodies 96, the inner sheet 94, the outer sheet 92, and the outer sheet fold over 93. The belt elastic bodies 96 may extend in the transverse direction to provide a ring like elastic belt 40 when the front belt 84 and the back belt 86 are joined. At least some of the elastic bodies 96 extend in the transverse direction substantially parallel to each other. All of the elastic bodies 96 may extend in the transverse direction substantially parallel to each other. Such an article may be economically made. The front and back belt 84, 86 each may have transversely continuous proximal and distal edges, the proximal edge 90 being located closer than the distal edge 88 relative to the longitudinal center of the article. The elastic bodies 96 may be disposed in the same or different denier, interval, and force between the front and back, as well as in different longitudinal positions of the belt.

The front and/or back belt 84, 86 may be treated such that certain of the area overlapping the front and/or back waist panel 52, 54 of the core chassis 38 are removed of elasticity. Removal of elasticity from a certain area of the front and/or back waist panel 52, 54 may be advantageous when they overlap the absorbent core 62, in that elasticity in the overlapping area may cause bunching of the absorbent layer or any of the layers in the absorbent core 62 and interfere with close fit of the core chassis 38 to the wearer. In one embodiment, at least a portion of, or at least 10% of, or at least 20% of, or at least 30% of, the elasticity of; at least one of, or at least half of, or at least two thirds of, the elastic bodies are removed in the region overlapping with the front and back waist panels 52, 54 of the core chassis 38. Referring to FIG. 2, the entire area where the elastic bodies 96 overlap with the absorbent core 62 may be removed of its elasticity as in the front belt 84. Alternatively, as seen in the backbelt 86, the elastic bodies 96 overlapping the absorbent material non-existing region 61 and toward the distal edges of the absorbent core 62 may be disposed in active elasticity for good fit of the core chassis 38. This may be advantageous in preventing leakage.

Referring to FIG. 2, the transverse width LW of the back belt 86 in the uncontracted condition may be the same as the transverse width of the front belt 84 of the same condition. Such an article may be economically made.

The longitudinal length LB of the back belt 86 between the back distal edge 88 and the back proximal edge 90 along its entire width LW of the back belt 86 may be approximately the same as the longitudinal length LF of the front belt 84 between the front distal edge 88 and the front proximal edge 90. In such configuration, the seams 32 close the front and back belt 84, 86 side edges 89 of the same length for forming the article. Such an article may be economically made.

The back belt 86 may have a greater longitudinal length LB between the back distal edge 88 and the back proximal edge 90 along its entire width LW of the back belt 86 in the transverse direction than the longitudinal length LF of the front belt 84 between the front distal edge 88 and the front proximal edge 90 (FIGS. 1 and 2). In such configuration, when the absorbent article is assembled to form the waist opening and the leg openings, the absorbent article 20 is folded along the transverse centerline T1 such that the front distal edge 88 is aligned with the back distal edge 88. The front side edge 89 is also aligned with a portion of the back side edge 89. Then the front belt 84 and the back belt 86 are joined at the front and back side edges 89 at the seams 32. The front and back proximal edges 90, however, may not be aligned to one another. The back proximal edge 90 may be disposed longitudinally closer than the front proximal edge 90 relative to the transverse center line T1 such that the proximal portion of the back side panel 82 extends toward the crotch panel 56 of the core chassis 38 beyond the front proximal edge 90. The side edge of the proximal portion of the back side panel 82 may not be joined to anywhere and free from attachment. Thus, the proximal portion of the back side panel 82 provides a buttock cover 95 as in FIG. 1.

The elastic belt region 40 may be closely associated with the function and quality of the article, thus materials and dimensions for forming the elastic belt region 40 are carefully selected by the manufacturer for providing the desirables for the article. Of high interest is to make the absorbent core 62 as less conspicuous as possible for providing an undergarment-like appearance and feel, while also maintaining sufficient containment capacity. The appearance and feel of the back elastic belt region 86 may represent the overall integral impression of the article to the user. The user may be the wearer or the caregiver. Referring to FIG. 2, for the belt-type pant, the back belt 86 matches the back elastic belt region 86, however, only the length matching the longutidinal length of the front belt LF is considered the tested areas in the measurement below. Without being bound by theory, it is believed that an overall integral impression for the absorbent article may be provided by minimizing the caliper difference of the maximum caliper and the minimum caliper of the middle tested area of the back elastic belt region 86. Namely, according to the measurements herein which measures the caliper of the back elastic belt region 86 of the article along the longitudinal centerline L1, the tested area of the back elastic belt region 86 of the absorbent article of the present invention has a maximum caliper, MaxBC, and a minimum caliper, MinBC, the difference between the MaxBC and the MinBC being no greater than about 5 mm, or no greater than about 3.5 mm, or no greater than about 3 mm. Further, the back elastic belt region 86 of the absorbent article of the present invention may have a ratio of MaxBC to MinBC of no greater than about 2.2, or no greater than about 2, or no greater than about 1.7. The back elastic belt region 86 of the absorbent article of the present invention may have a MaxBC of no greater than about 8 mm, or no greater than about 7 mm.

Without being bound by theory, it is believed that an overall integral impression for the absorbent article may be provided by minimizing the caliper difference of the middle tested area of the back elastic belt region 86 along the longitudinal axis, and the side tested area of the back elastic belt region 86 which is 80 mm away in the lateral direction from the middle tested area, wherein the middle tested area and the side tested area which have the same distance from the waist opening 88 are compared. The side tested area 80 mm away in the lateral direction from the longitudinal center line is typically an area wherein the absorbent core 62 is no longer present, and thus represent a region wherein the caliper of the back elastic belt region 86 which is expected to be significantly lower compared to that in the middle tested areas where the absorbent core 62 is present. According to the measurements herein, the caliper of the middle tested area and the side tested area which have the same distance from the waist opening 88 are compared to obtain a caliper delta. Among the caliper delta thus obtained, the maximum caliper delta, ΔMaxBC, is identified. According to the measurements herein, the ΔMaxBC of the present invention is no greater than about 7 mm, or no greater than about 6 mm, or not greater than about 5 mm.

In order to meet the caliper profile requirements of the belt elastic belt region 86 as described above, while also maintaining sufficient containment capacity, the materials for making the laminate of the belt elastic belt region 86 may be made lofty to the touch, while providing the core chassis 38 as thin as possible utilizing highly absorbent material.

The outer sheet 92 for forming the elastic belt region 40 may have a certain material thickness to provide the lofty undergarment-like appearance and feel, for example, at least about 0.25 mm, or at least about 0.3 mm. Providing the outer sheet 92 have a lofty feel may further contribute in alleviating the caliper difference perception between regions of the back belt. The material thickness herein is related to materials obtained from a finished product according to the "Preparation for Thickness and Basis Weight" below and measured by "Base caliper method—ASTM D 654 Standard Test Method for Thickness of Paper and Paper Board" with modification of the loading to 500 Pa. Suitable for the outer sheet 92 of the present invention include: hi-loft nonwoven, air-through carded nonwoven, and spunbond nonwoven made of crimping fiber made through core eccentric bicomponent filament or side by side bicomponent filament, preferably air-through carded nonwoven. Non-limiting examples of materials suitable for the outer sheet 92 include: 20-50 gsm air-through carded nonwoven made of less than 15 nm diameter PE/PET bi-component staple fiber, such as those with a tradename of FJ206 available from Dayuan, Beijing China.

The inner and outer sheets 92, 94 may be the same or different material, and selected to provide characteristics such as breathability, softness, cushiony feel, loftiness, and combinations thereof, depending on the desirables of the resulting article. The inner and outer sheets 92, 94 may have the same or different basis weight, stiffness, texture or any combination thereof. The outer sheet 92 may have higher basis weight than the inner sheet 94 for providing the favorable tactile acceptance as discussed above, while controlling cost.

Suitable for the inner sheet 94 of the present invention include: 10-40 gsm soft nonwoven, spunbond nonwoven with filament additive slip agent, spun high-loft nonwoven or air-through carded nonwoven, preferably spun high-loft nonwoven.

The material for the outer cover layer 42 may be selected to provide characteristics such as breathability, softness, cushiony feel, loftiness, and combinations thereof, depending on the desirables of the resulting article. The outer cover layer 42 may be made of the same material as the outer sheet 92 to provide integral aesthetic and tactile senses for the article. By "the same material", what is meant is that the nonwoven has the same type of filament in shape, composition, diameter difference of no more than 2 nm, and basis weight difference of no more than 2 gsm. Such comparison of the materials is made by analyzing the materials by SEM and FTIR measurements as detailed below. The basis weight herein is related to materials obtained from a finished product according to the "Preparation for Thickness and Basis Weight" below and measured by "Basis weight—ASTM D 756 Practice for Determination of Weight and Shape Changes of Plastics Under Accelerated Service Conditions".

The force provided by the belt elastic region, or the force provided by the back belt relative to the front belt, may influence the softness perception of the belt elastic region. The force provided by the front belt may be configured to be greater than the force provided by the back belt.

As mentioned above, the core chassis 38 may be made as thin as possible utilizing highly absorbent material, in order to meet the caliper profile requirements of the back belt elastic region 86.

To provide such a core chassis 38, the absorbent core 62 may comprise an absorbent layer including absorbent materials having a high retention capacity, such as superabsorbent polymers, and substantially cellulose free. The superabsorbent polymers may be profiled in distribution, such that materials in the vicinity of the urinating points are high in basis weight, while less so in other areas, so as to keep the caliper of the absorbent core 62 as low as possible in the regions nearby the absorbent material non-existing region 61, such that the transition of caliper from the waist opening to the region having the absorbent core 62 is gradual rather than sudden. The acquisition layer of the absorbent core 62 may also be profiled such that a gradual caliper transition profile is made nearby the absorbent material non-existing region 61. The distal edge of the acquisition layer may be proximal than the distal edge of the superabsorbent polymers existing region. Namely, the superabsorbent polymers existing region may match the longitudinal periphery of the absorbent core 62, thus extend beyond the longitudinal periphery of the acquisition layer.

Effective usage of artwork may also contribute in providing the overall integral impression of the article and alleviate the appearance of discrete parts which form the absorbent article. Referring to FIGS. 4 and 7A-7C, the article of the present invention may have a chassis artwork 30A which is disposed on the core chassis 38 and a belt artwork 40A which is not disposed on the core chassis 38. For providing attractive artwork in an economical manner, a chassis artwork 30A may be printed on the garment facing side of the backsheet 60. Such chassis artwork 30A, however, may not extend to the vicinity of the waist opening or leg openings. The waist opening and leg openings are areas where an undergarment would typically have some visual accent, such as elastics disposed at the edge of the waist and leg openings, piping of elastics, laces, etc. As such, in addition to the chassis artwork 30A, a belt artwork 40A may be provided. The belt artwork 40A may be provided by printing on the sheets 92, 94 for making the elastic belt 40, by disposing a colored web of a predetermined shape, or by disposing colored elastics or adhesives in the desired regions. With the combination and coordination of the chassis artwork 30A and the belt artwork 40A, an appearance similar to an undergarment may be provided. For example, in FIG. 4, coloring of the waist end is provided by the belt artwork 40A, and coloring of the leg opening is provided by the combination of the belt artwork 40A toward the proximal edge of the belt and the chassis artwork 30A artwork toward the lateral side edges, and characters are depicted in the center of the article by the chassis artwork 30A. As in FIGS. 7A-7C, there may be graphical elements coming from the chassis artwork 30A that are similar to those from the belt artwork 40A that are coordinated with each other to provide a holistic integral appearance. These graphical elements include, but are not limited to, shapes, patterns, colors, and combinations thereof. For example, in FIGS. 7A-7C, there are provided diamond shape elements and bear-like characters from both the chassis artwork 30A and belt artwork 40A; which cooperatively provide an integral appearance.

Referring to FIG. 3, for the belt-type pant, when the front and back belts 84, 86 are discontinuous with one another in the crotch region 30, and the outer cover layer 42 is the garment-facing surface in the crotch region 30. The outer cover layer 42 may extend only partly in the longitudinal direction of the front waist panel 52 and the back waist panel 54 to leave the distal parts of the front waist panel 52 and the back waist panel 54 free of the outer cover layer 42. Namely, the longitudinal length of the outer cover layer 42 may be longer than the longitudinal length of the crotch panel 56 and shorter than the longitudinal length of the backsheet 60. By such configuration, the distal parts of the front waist panel 52 and the back waist panel 54 are devoid of the outer cover layer 42, further contributing to avoid sudden increase of caliper in this region of the elastic belt region 40. Such configuration may also provide better breathability to the overall article, and cost saving of the outer cover layer 42 material. Accordingly, looking at the layers of elements between the garment facing surface and the backsheet of the center chassis 38 of FIG. 3, there exists a transitional region 34 disposed on the waist panel 52 where the outer cover layer 42 is present. The longitudinal length of the transitional region 34 may be made as short as possible, for example, less than about 20 mm, or less than about 15 mm, or less than about 10 mm. Further, adhesive may be applied on the entire area of the transitional region 34, or the entire area leaving no more than up to 5 mm, in the longitudinal direction, from the distal edge of the transitional region 34. For providing attractive artwork for an absorbent article in an economical manner, printing may be provided on the garment facing side of the backsheet 60. By providing the transitional region 34 as short as possible, applying adhesive to the transitional region 34 to enhance transparency, or simply avoiding displaying artwork in the transitional region 34, compromised appearance of the artwork over different layers of material between the artwork and the observer may be avoided. Thus, overall integral impression may be enhanced.

Figure 4:
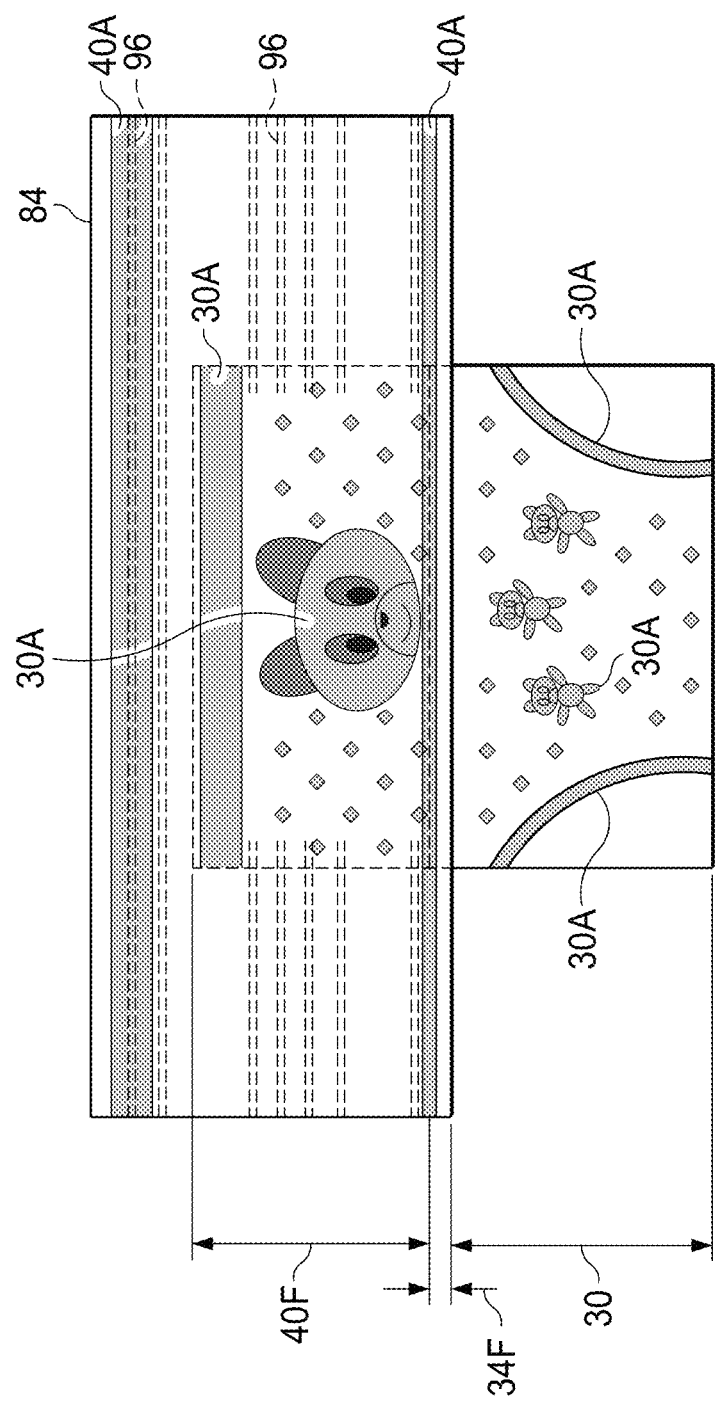
FIG. 4 is a partial schematic plan view of one embodiment of a wearable article of the present invention showing the garment facing surface.

Referring to FIGS. 2-4, the belt artwork 40A may be printed on the garment facing surface of the inner sheet 94 or the body facing surface of the outer sheet 92, and the chassis artwork 30A may be printed on the backsheet 60. The chassis artwork 30A may be printed in the front chassis artwork region 40F or back chassis artwork region 40B. By printing the artwork in these specific layers and the specific artwork regions, the number of layers between the garment facing surface and the printing of the belt artwork 40A and chassis artwork 30A may be made equal, thus the appearance difference may be alleviated. The opacity difference between the outer sheet 92 and the outer cover layer 42 may be minimized by selecting the layers to match the opacity, or by disposing the same material.

As mentioned above, the front belt may have a longitudinal length of LF; and the back belt may have a longitudinal length of LB, and the outer sheet fold over 93 is formed by folding the outer sheet material at the distal edge 88 of the front and back belts. The front outer sheet fold over 93 may have a longitudinal length of at least about 0.3 LF, or from about 0.3 LF to about 0.7 LF, or from about 0.5 LF to about 0.7 LF. The back outer sheet fold over may have a longitudinal length to match the length of the front outer sheet fold over. Namely, the back outer sheet fold over may have about the same length as the front outer sheet fold over.

As mentioned above, the elastic belt region 40 exhibits elasticity due to the plurality of elastic bodies 96 configured to stretch the front and back elastic belt regions in the transverse direction, wherein the elastic bodies 96 are adhered to the inner and outer sheets 92, 94. Tensile stress of the elastic belt region 40 may be adjusted by one or more of the following methods; 1) elongation rate of the elastic body 96; 2) density (dtex) of the elastic body 96; 3) longitudinal interval of multiple elastic bodies 96; and 4) effective length of elasticity of the elastic body 96 in the transverse direction. By elongation, "0% elongation" is meant the original length of the elastic body 96. Some elastics may be disposed to impart higher tensile stress in certain regions. Such one or more elastics of higher tensile stress may be disposed in an array of 2-4 elastic strands having an interval within the array of between 2-4 mm. The array may be disposed on the front belt between the longitudinal length of from about 0.5 LF to about 0.85 LF from the waist opening. The array may be disposed on the back belt between the longitudinal length of from about 0.25 LF to about 0.5 LF from the waist opening.

The articles of the present invention provides smooth transition of the back belt from the waist opening to the region having an absorbent core, perception of even thickness at the back side of the article, which may lead to the perception of being soft around the waist, fit like underwear, overall softness, and overall product quality.

1. Preparation for Thickness and Basis Weight

The following sampling procedures are taken for measuring thickness and basis weight of a material used in a finished product.

To obtain a sample from a finished article, when available, an area free of deformation or wrinking is selected. For the belt elastic region 40, when available, area where the elasticity is deactivated is selected. The outer sheet 92, inner sheet 94, or outer cover layer 42 is separated from the other components such as belt laminated nonwoven layers, or backsheet film by techniques such as applying "Quik-Freeze®" type cold spray, or other suitable methods that do not permanently alter the properties of the nonwoven composition. The technical face-side is the surface intended to be used as the garment-facing surface for the outer sheet 92 or outer cover layer 42, and the body-facing surface for the inner sheet 94. Care should be taken to prevent stretching of the nonwoven composition during the separation process. A 100 mm by 100 mm square shape is cut out using a cutter and a 100 cm$^2$ die for obtaining the sample.

For measuring the basis weight, any remaining adhesive is removed from the sample by the following steps using Tetrahydrofuran (THF) as solvent.

1. In a hood, transfer 1 liter of THF into the 3-4 liter beaker
2. Submerge sample in the 1 liter of THF
3. Place beaker on shaking table and stir gently for 15 minutes and keep solution with sample sit for 5 additional minutes
4. Take sample out of THF solution, and carefully squeeze THF solution out of sample.
5. Let sample air dry in hood for a minimum of 15 minutes Samples are obtained from ten (10) finished products from the same package and cut out from the same area of each article, for each set of measurement. Samples are pre-conditioned in a room maintained at about 23±2° C. and about 50±5% relative humidity, for at least 2 hours prior to testing.

2. MaxBC and MinBC 2-1. Whole Article Force Measurement

Force is measured using an Electronic Tensile Tester with a computer interface such as the MTS Criterion C42 running TestWorks 4 Software (available from MTS SYSTEMS (CHINA) CO., LTD) or equivalent instrument. A load cell is selected so that force results for the samples tested will be between 10% and 90% of capacity of the load cell used. The instrument is calibrated according to the manufacturer's instructions. All testing is performed in a room maintained at 23±2° C. and 50±5% relative humidity.

Figure 5:
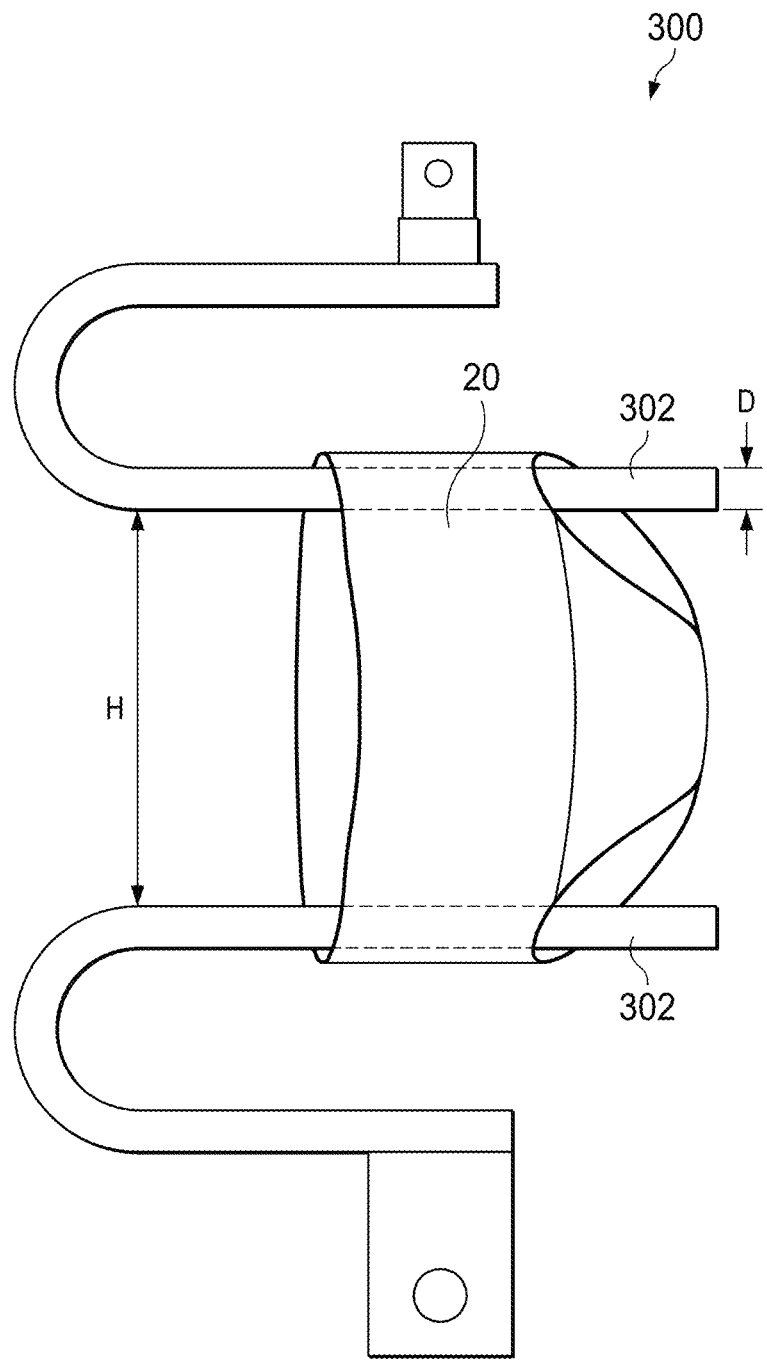
FIG. 5 is a schematic view of an example of a hanger-type sample holding fixture according to the "Whole Article Force Measurement".

The tensile tester is fitted with hanger-type sample holding fixtures 300 as shown in FIG. 5. Each fixture comprises a rigid linear rubber-coated horizontal bar section 302 to prevent sample slippage during testing. The outer bar diameter (including the rubber coating) of the horizontal bar sections is 10.0 mm. The central axes of the horizontal bar sections 302 are configured to remain parallel and in the same vertical plane throughout the test procedure. The gauge circumference is determined by the following equation:

$$\text{Gauge Circumference} = 2 \times (H + D + \pi D/2)$$

where H is the vertical gap between the horizontal bar sections 302, and D is the outer diameter of the bar.

The instrument is set up to go through the following steps:

| | |
|---|---|
| Crosshead Speed | 254.0 mm/min |
| Final Load Point | 19.61N |
| Hold Time | 0 |
| Number of Cycles | 1 |
| Data Acquisition Rate | 50 Hz |

A sample article 20 is inserted onto the upper horizontal bar section 302 so that the bar passes through the waist opening and one leg opening of the article. The crosshead is raised until the specimen hangs above the lower bar and does not touch the lower bar 302. The load cell is tared and the crosshead is lowered to enable the lower bar 302 to be inserted through the waist opening and other leg opening without stretching the article. The article is adjusted so that the longitudinal centerline L1 of the article is in a horizontal plane halfway between the upper and lower bars 302. The center of the side portion in contact with the bar 302 is situated on the same vertical axis as the instrument load cell. The crosshead is raised slowly while the article is held in place by hand as necessary until the force is between 0.05 and 0.1N, while taking care not to add any unnecessary force. The gauge circumference at this point is the Initial Gauge Circumference. The test is initiated and the crosshead moves up at 254 mm/min until a force of 19.6N is attained, then the crosshead immediately returns to the initial gauge circumference at the same speed. The maximum circumference at 19.6N and the force at 70% stretch circumference during the extension segment of the test are recorded.

$$\text{Circumference (mm)} = 2 \times (H + D + \pi D/2)$$

The maximum circumference at 19.6N is defined as the Full Circumference (mm). The 70% stretch circumference is defined as the Full Circumference×0.7. Five samples are analyzed and their average 70% stretch circumference is calculated and reported to the nearest 1 mm.

2-2. 3D Macroscope Measurement

Figure 6:
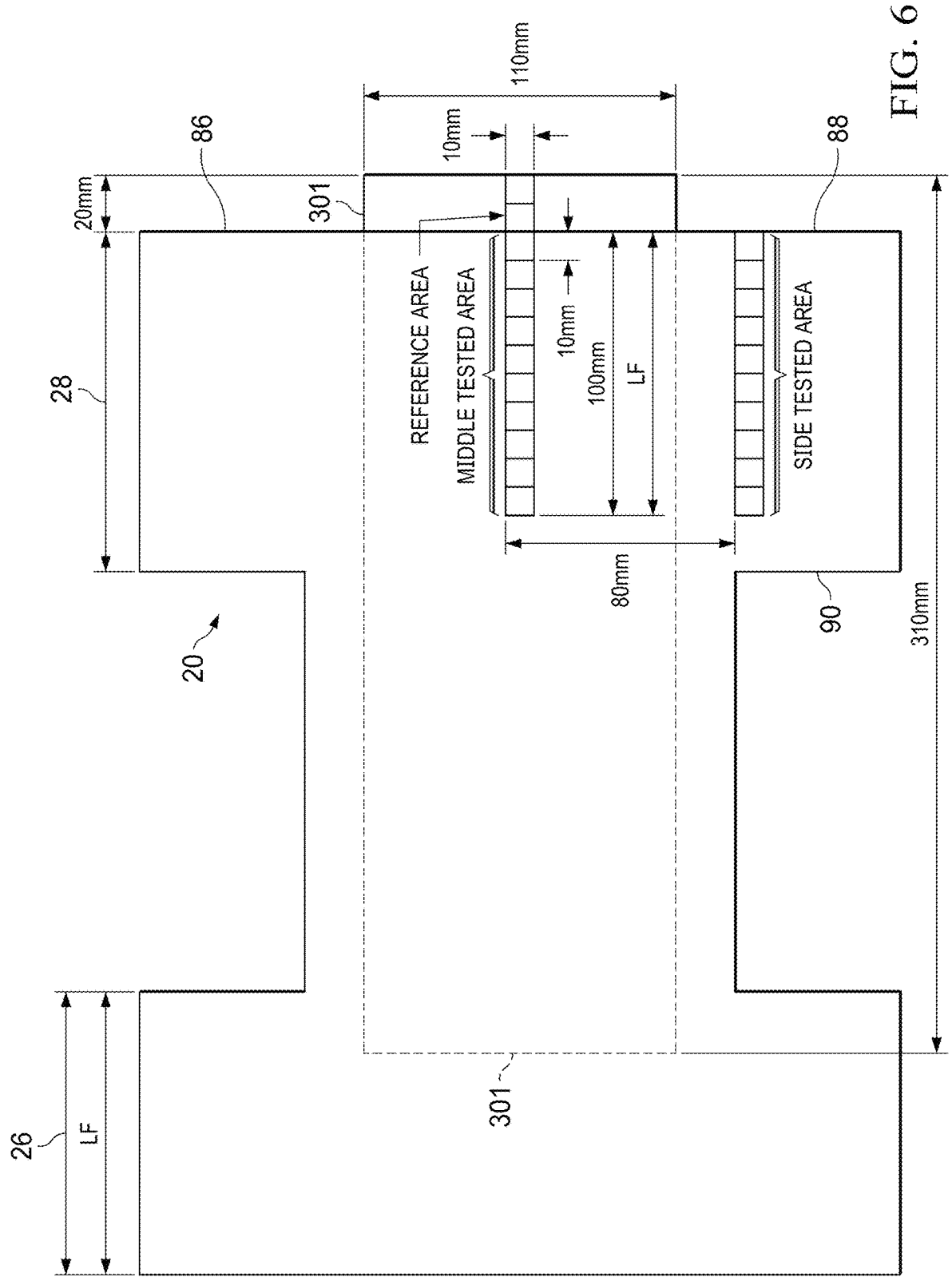
FIG. 6 is a schematic view of an example of a sample preparation according to the "3D Macroscope Measurement".
Figure 7C:
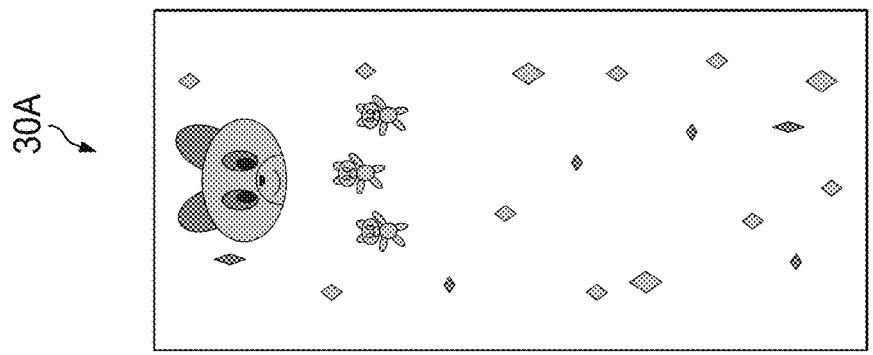
FIG. 7A-7C are schematic plan views of another embodiment of a wearable article of the present invention showing the garment facing surface.
Figure 7B:
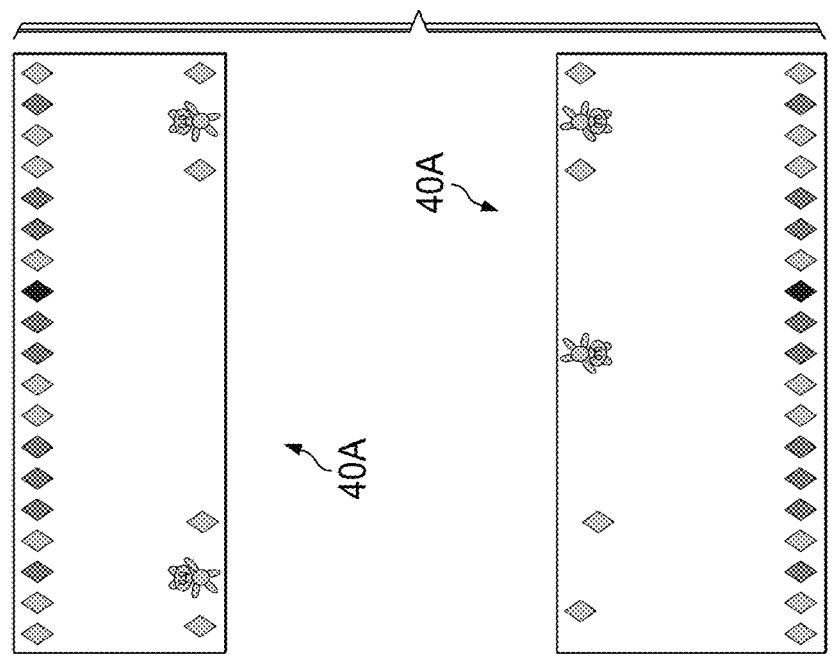
Figure 7A:
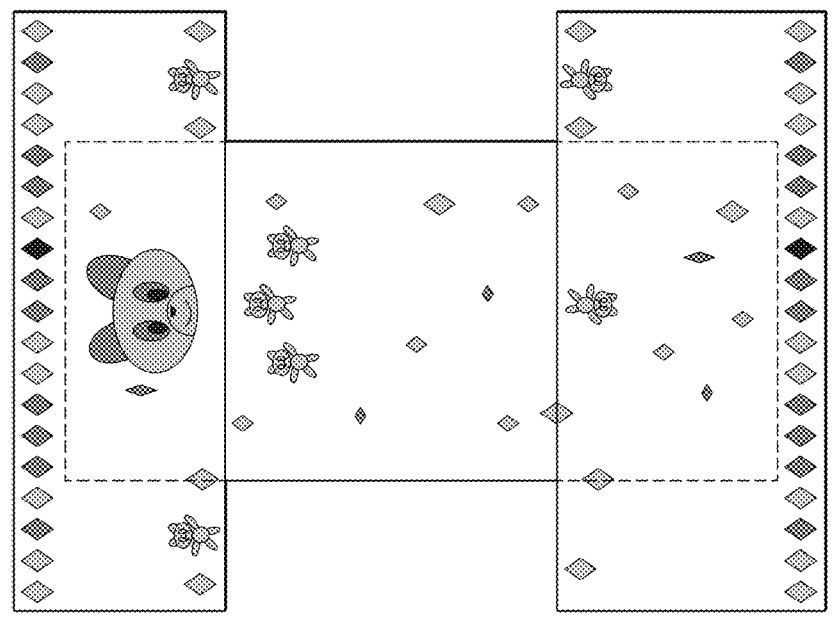

To obtain a sample for this measurement, the side seams 32 of an article are opened, and the back elastic belt region 86 is attached on surface of a 310 mm by 110 mm non-transparent backboard 301 by hook material, or double side tape material, as in FIG. 6. The 310 mm length of the backboard 301 is suitable for a baby diaper, however, may be extended further for securely attaching the back elastic belt region 86 of the article. When attaching, the back elastic belt region 86 of the sample is stretched to 50% of the average 70% Stretch Circumference as obtained in the "Whole Article Force Measurement" above. The sample's garment-facing surface faces the backboard 301. The distance between the upper edge of the backboard 301 and article's back belt distal edge 88 is adjusted to 20 mm.

To obtain the maximum caliper MaxBC and the minimum caliper MinBC, the lateral center of the sample is attached to the backboard 301. What is measured is the height difference between the reference area and other areas that are set on the image captured using a 3D Macroscope with a computer interface such as Keyence VR-3200 running VR-3000 Series Software, or equivalent instrument. Start the VR-3000 series software, and select the Viewer application. Place 310 mm by 110 mm acrylic board with sample attached on the XY stage of the 3D Macroscope for observation and measurement. The instrument is set up to go through the following steps:

| | |
|---|---|
| Measurement mode | Standard mode of one-shot 3D |
| AF | Enabled |
| Brightness | 100 |
| Auto stitching | Enabled |
| Stitching area specification method | Simple specification: Add stitching area (120 mm width × 18 mm height) along with the longitudinal centerline of the sample, which starts from the upper edge of the backboard. |

The caliper profile of the sample article along the longitudinal center line L1 is determined by the following equation wherein "n" is the specified tested area:

$$\text{Sample caliper}_n = \text{Average step height}_{tested\ area-n} - \text{Average step height}_{reference\ area}$$

Set a reference area and a comparison area at the measurement position on the image displayed in the average step height measurement window as below. The tested area starts at the back belt distal edge 88 and ends at an imaginary line running in the transverse direction between the proximal edges of the side seams. As in FIG. 6, when the back belt 86 is longer than the front belt 84, the tested area matches the longitudinal length LF of the front belt 84. In the example below, the longitudinal length LB of the back elastic belt region 86 was 120 mm, but the tested area LF was 100 mm. FIG. 6 is depicted as if the core chassis and front belt 84 are in a flat uncontracted condition, however, this is merely for describing the dimensions LF and LB. The remainder of the sample article, except for the back elastic belt region 86, need not be stretched upon measurement.

| | |
|---|---|
| Reference area (10 mm × 10 mm square) | Upper part of backboard without sample article attached |
| Tested area (Plurality of 10 mm × 10 mm squares) | 10 of selected areas are connected, in the middle of the sample article and along with the longitudinal centerline of the sample article, which starts from the upper edge of the sample article |

Five samples are calculated and the sample caliper of the 10 selected areas are reported to the nearest 0.1 mm (hereinafter, "middle tested area caliper"). Among the middle tested areas, the maximum "Sample caliper" obtained from an average of five samples is the maximum caliper MaxBC; and the minimum "Sample caliper" obtained from an average of five samples is the minimum caliper MinBC.

To obtain the maximum caliper delta, $\Delta$MaxBC, the sample is attached to the backboard 301 such that the portion 80 mm away from the longitudinal axis matches the center of the backboard 301, with the distance between the upper edge of the backboard 301 and article's back belt distal edge 88 adjusted to 20 mm, as in FIG. 6. What is measured is the height difference between the reference area and other areas in the side tested area using the same conditions above.

Five samples are calculated and the sample caliper of the 10 selected areas are reported to the nearest 0.1 mm (hereinafter, "side tested area caliper"). The side tested area caliper of five samples are averaged for each side tested area, respectively. The average side tested area caliper is subtracted from the average middle tested area caliper of the same distance from the distal edge 88. Among thus obtained values, the greatest absolute value is the maximum caliper delta, $\Delta$MaxBC.

Scanning Electron Microscope (SEM) and Fourier Transform Infrared Spectroscopy (FTIR) Tests 3-1. Sample Preparation To obtain a nonwoven raw material sample, lay the material flat on a bench with the technical face-side upward, and a 20 mm (along machine direction) by 20 mm (in the perpendicular direction of machine direction) square shape of sample are cut using scissor. The technical face-side is the surface intended to be used as the garment-facing surface for the outer sheet 92 or the outer cover layer 42, and the body-facing surface for the inner sheet 94.

To obtain a sample from a finished article, the outer sheet 92 and inner sheet 94 is separated from the other components such as belt laminated nonwoven layers, or back sheet film by techniques such as applying "Quik-Freeze®" type cold spray, or other suitable methods that do not permanently alter the properties of the nonwoven composition. The technical face-side is the surface used as the garment-facing surface for the outer sheet 92 or the outer cover layer 42. The area where the elasticity of the belt elastic region is deactivated is preferred. A 20 mm by 20 mm square shape is cut out using scissors for obtaining the sample. For those articles having deactivated areas in the elastic belt region that are smaller than 20 mm by 20 mm, a 20 mm by 20 mm square shape is cut out using scissors, and the elastics are separated from the samples by techniques such as applying "Quik-Freeze®" type cold spray, or other suitable methods that do not permanently alter the properties of the nonwoven composition. Five samples are cut from the same portion of finished products from the same package for measurement.

3-2. Scanning Electron Microscope (SEM)

Scanning Electron Microscope images are taken using Hitachi TM3000 Bench-top SEM running Hitachi 3D-viewer software, or equivalent instrument. The 20 mm by 20 mm sample is submerged in liquid nitrogen and an edge is fractured with a razor blade (stainless steel coated, single edge industrial blades, 62-0165). Fractured samples are adhered to SEM mounts using double-sided Cu tape. The samples are sputter Au coated and are viewed in the SEM. The SEM images are acquired from top view, and x-section view. Fiber diameter and width measurements are made using the manual line tool in SEM operating software.

3-3. Fourier Transform Infrared Spectroscopy (FTIR)

Based on the SEM images described above, the structure of the material is observed. For samples made of mono-component fibers, all measurements are conducted by FTIR-ATR under the following conditions. A small piece (enough to cover ATR crystal) of the sample is enough to do the measurement. Apply proper and consistent pressure on top of samples using ATR pressure arm.

| Instrument | PerkinElmer Spotlight 400 Fourier Transform Infrared Spectroscopy, or equivalent instrument |
|---|---|
| Collection mode | ATR-FTIR |
| Wavenumber range | 4000-600 $cm^{-1}$ |
| Accumulation | 16 scan |
| Spectral resolution | 4 $cm^{-1}$ |

For samples made of mixed fibers or multi-component fibers such as sheath-core, side-by-side structures etc., with the aim to understand each type of fiber in the mixed fiber or each distinct part of the multi-component fiber, a few fibers are separated from each sample under the stereoscope, and are squashed up by diamond cell to be measured by Micro-IR under the following conditions. Material identification is conducted using KnowItAll informatics system, or other reference spectra library.

| Instrument | Nicolet iN10, or equivalent instrument |
|---|---|
| Wavenumber range | 4000 to 700 $cm^{-1}$ |
| Accumulation | 64 scan |
| Spectral resolution | 4 $cm^{-1}$ |

EXAMPLES

Examples A-F having the structure of a pant type absorbent article obtained as such are subject to measurements as described above, and consumer acceptance tests described below.

Example A

A Size 4 belt-type pant article with Lot No. SRB option 3, 2104 2016 6 112 4499 having the configuration of FIG. 2 and elastic profile of Table 1 below, with the outer sheet and outer cover layer made by tradename FJ206 available from Dayuan, Beijing China (20 gsm air-through carded nonwoven with 15 μm diameter PE/PET bicomponent fiber) and the inner sheet made by tradename HY15015-MALAYSIA-V2 available from Fibertex (15 gsm PP spunbond nonwoven). The absorbent core contains an absorbent layer which is substantially cellulose free. There are both chassis artwork 30A printed on the backsheet and belt artwork 40A printed on the outer sheet 92.

Example B

A Size 4 belt-type pant article with Lot No. SRH, 200420166 111 449979 having the same configuration as Example A except the outer sheet made by dual 17 gsm PE/PP bicomponent spunbond nonwoven available from Fibertex, and the outer cover layer made by 25 gsm PP spunbond nonwoven with melt additive, available from Pegas. There is chassis artwork 30A printed on the backsheet but no belt artwork 40A.

Example C

A Size 4 uni-body type pant article sold by the tradename of "Huggies Platinum Pants" with Lot No. 20160917 purchased by China E-com shop in November 2016. There is chassis artwork 30A printed on the backsheet but no belt artwork 40A.

Example D

A Size 4 uni-body type pant article sold by the tradename of "Merries Pants" with Lot No. 20160329 purchased by China E-com shop in November 2016. There is chassis artwork 30A printed on the backsheet but no belt artwork 40A.

Example E

A Size 4 belt-type pant article sold by the tradename of "Anerles Gold Pants" with Lot No. 20160520 purchased by China E-com shop in November 2016. There is chassis artwork 30A printed on the backsheet but no belt artwork 40A.

Example F

A Size 4 uni-body type pant article sold by the tradename of "Merries Pants" purchased in the Peoples Republic of China during October to December 2015 having Lot #20150222. There is chassis artwork 30A printed on the backsheet but no belt artwork 40A.

TABLE 1

| | | dtex/elongation %/ number of elastic bodies |
|---|---|---|
| Front | 0-25% LF from waist opening | 540dtex/150%/4 |
| | 25-50% LF from waist opening | 540dtex/150%/2 |
| | | 540dtex/150%/2 tummy cut |
| | 50-85% LF from waist opening | 940dtex/210%/8 tummy cut |
| | 85-100% LF from waist opening | 540dtex/150%/2 tummy cut |
| Back | 0-25% LF from waist opening | 540dtex/150%/4 |
| | 25-50% LF from waist opening | 940dtex/130%/4 |
| | 50-85% LF from waist opening | 540dtex/210%/2 |
| | | 540dtex/210%/4 tummy cut |
| | 85-100% LF from waist opening | 540dtex/210%/2 tummy cut |

(*1) tummy cut in Table 1 refers to removal of elasticity at the central area of elastic strands which overlap the central chassis 38, resulting in 66% effective length of elasticity.

TABLE 2

| | Example | | | | |
|---|---|---|---|---|---|
| | A | B | C | D | E |
| MinBC (mm) | 4.1 | 3.8 | 3.8 | 4.7 | 2.6 |
| MaxBC (mm) | 6.7 | 5.2 | 10.2 | 10.4 | 8.4 |
| Difference between MinBC and MaxBC (mm) | 2.6 | 1.4 | 6.4 | 5.7 | 5.8 |
| Max/Min ratio | 1.64 | 1.37 | 2.68 | 2.21 | 3.23 |
| Material caliper of outer sheet (mm) | 0.33 | 0.22 | 0.26 | 0.32 | 0.33 |
| ΔMaxBC (mm) | 2.7 | 3.2 | 8.2 | 9.5 | 7.1 |

Consumer Acceptance Test
Test 1

30 panelists who were caregivers of babies using Size 4 pant diapers at a frequency of minimum 3 pads per day, and having a mixture of usage experience of major brands: "Merries", "Huggies Gold" and "Pampers"; were recruited. There were equal number of caregivers of boy and girl babies. Each panelist was given 9 test products altogether on a table. Among the 9 test products, Examples A, B, E and F were included. The panelists were asked to sort the 9 products on to the scale 1-10 on the table for each question. The rating score of 30 panelists were averaged for the report as in Table 3. (The remainder of the 9 products except Examples A, B, E, and F were those not listed in the Examples list above, and were; "Huggies Gold Pants", "Huggies Silver Pants", "Mammy Poko Pants", "Anerle Silver Pants", and "Goon Pants", all purchased in the Peoples Republic of China during October to November 2015.) The Samples had different lot numbers as follows: Sample A: hand-made prototype EUS-069-14 Opt 12, Sample B: EUS-069-14, SRL Opt10, and Sample E: 20171025 for boys, 20171020 for girls.

TABLE 3

| Values/Questions | A | B | E | F |
|---|---|---|---|---|
| Overall liking | 8.3 | 6.7 | 7.4 | 8.4 |
| Underwear like | 8.4 | 5 | 7.5 | 7.9 |

Example D in Table 2 above is an updated product of Example F in Table 3. In view of the similarity in structure, it is believed that the caliper profiles of Example F would be very similar to that of Example D.

Test 2

Two groups of respondents (87 and 30 respectively) who were caregivers of babies using Size 4 pant diapers at a frequency of minimum 3 pads per day, and having a mixture of usage experience of major brands: "Merries", "Huggies Platinum", "Moony", "Goon" and "Pampers"; were recruited. Each panelist was given 2 types of test products to use sequentially—either sample A & D (half used A first and half used D first) or sample A & B (half used A first and half used B first). After use, the panelists were asked to rate the test products on to the scale of 0-100 for each question. The rating score of two products used were averaged for the report as in Table 4. The Samples had different lot numbers as follows: Sample A: 20170425, Sample B: 20161206, and Sample D: 20160402 purchased in the Peoples Republic of China during October to November 2016.

TABLE 4

| | Values/Questions | | | |
|---|---|---|---|---|
| | Comparison of A and D N = 87 | | Comparison of A and B N = 30 | |
| Example | A | D | A | B |
| Overall Rating | 77s (*2) | 65 | 77 | 73 |
| Even thickness at the back of diaper pants | 76s (*2) | 68 | 81s (*2) | 69 |
| Fit like Underwear | 80s (*2) | 70 | 79 | 77 |
| High Quality | 78s (*2) | 71 | 76 | 73 |
| Being Soft overall | 80s (*2) | 73 | 80 | 78 |

(*2) Statistically significant at risk of 10%

In Test 1, the Inventive Example A which meets the parametric requirements of the present invention have high acceptance for "overall liking" and highest acceptance of "underwear like" while the other examples which do not meet the parametric requirements of the present invention are slightly to significantly inferior in consumer acceptance in at least some aspect. In Test 2, the Inventive Example A has a higher overall rating compared to Examples B and D, respectively, and has significantly better acceptance than both Examples in view of "Even thickness at the back of diaper pants". Further, in view of comparison between Example D, Inventive Example A has significantly better acceptance in view of "Fit like Underwear", "High Quality", and "Being soft overall". The parameters of the present invention provide a good predictability of consumer acceptance in view of tactile and aesthetic sense provided by the article.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." Further, every numerical range given throughout this specification includes every narrower numerical range that falls within such broader numerical range.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article continuous in a longitudinal direction and a transverse direction comprising a front elastic belt region, a back elastic belt region, a crotch region, a waist opening and two leg openings;
   the front and back elastic belt regions being a laminate comprising an inner sheet made of nonwoven fiber, and an outer sheet made of nonwoven fiber, and a plurality of elastic bodies configured to stretch the front and back elastic belt regions in the transverse direction, the outer sheet having a material caliper of at least about 0.25 mm at 500 Pa;
   the article further comprising a topsheet, a backsheet, and an absorbent core disposed between the topsheet and the backsheet; the absorbent core existing through the entire longitudinal dimension of the crotch region and extending at least partly in the back elastic belt region;
   the back elastic belt region including a region where the absorbent core is present having a maximum caliper, MaxBC, and the back elastic belt region including a region where the absorbent core is not present having a minimum caliper, MinBC, according to the measurements herein, wherein the difference between the MaxBC and the MinBC is no greater than about 5 mm.

2. The article of claim 1 wherein the ratio of the MaxBC to the MinBC is no greater than about 2.2.

3. The article of claim 1 wherein the MaxBC is no greater than about 8 mm.

4. The article of claim 1 wherein the back elastic belt region has a maximum caliper delta, ΔMaxBC, of no greater than about 7 mm, according to the measurements herein.

5. The article of claim 1 wherein the crotch region comprises an outer cover layer at the most garment facing side, and the outer cover layer is the same material as the outer sheet.

6. The article of claim 5 wherein the outer sheet is an air-through carded nonwoven made of crimping fiber made through core eccentric bicomponent filament, or side by side bicomponent filament.

7. The article of claim 1 wherein the absorbent core comprises an absorbent layer which is substantially cellulose free.

8. The article of claim 1 wherein the article comprises a core chassis and a ring-like elastic belt comprising a front belt and a back belt; the center of the front belt is joined to a front waist panel of the core chassis, the center of the back belt is joined to a back waist panel of the core chassis, and the remainder of the core chassis forms the crotch region, the front and back belt each having a left side panel and a right side panel where the core chassis does not overlap, and the transverse edges of the front belt and the back belt are joined by a seam to form a waist opening and two leg openings; wherein the front belt and the back belt are discontinuous of each other in the longitudinal direction;
wherein the front belt and the back belt forms the elastic belt region.

9. The article of claim 8 wherein the force provided by the front belt is greater than the force provided by the back belt.

10. The article of claim 8 wherein the front and back belt each have the plurality of elastic bodies running in the transverse direction, the inner sheet, the outer sheet, and an outer sheet fold over; the front and back belt each having transversely continuous proximal and distal edges, wherein the outer sheet fold over is an extension of the outer sheet formed by folding the outer sheet at the distal edge of the front and back belts.

11. The article of claim 10 wherein the front belt has a straight and transversely running proximal and distal edges, the front belt has a longitudinal length of LF; and the back belt has a straight and transversely running proximal and distal edges, wherein the front outer sheet fold over has a longitudinal length of at least about 0.3 LF, preferably the back outer sheet fold over has about the same length as the front outer sheet fold over.

12. The article of claim 8 wherein the core chassis comprises the outer cover layer at the most garment-facing side and a backsheet attached to the body-facing surface of the outer cover layer; wherein the longitudinal length of the outer cover layer is longer than the longitudinal length of the crotch region and shorter than the longitudinal length of the backsheet, the area on the front waist panel or the back waist panel where the outer cover layer is present forming a transitional region, preferably the longitudinal length of the transitional region being no more than about 10 mm.

13. The article of claim 8 wherein the elastic body is an elastic strand having a dtex of about 470 to about 1100, and at least some of the elastic stands are disposed in an array of 2-4 elastic strands having an interval within the array of between 2-4 mm, preferably the array disposed on one or both of:
  a) the front belt between the longitudinal length of from 0.5 LF to 0.85 LF from the waist opening; and
  b) the back belt between the longitudinal length of from 0.25 LF to 0.5 LF from the waist opening.

14. The article of claim 8 further comprising a belt artwork which is not disposed on the core chassis.

15. The article of claim 14 further comprising a chassis artwork which is disposed on the core chassis.

* * * * *